(12) United States Patent
Ayrenschmalz et al.

(10) Patent No.: US 10,070,775 B2
(45) Date of Patent: Sep. 11, 2018

(54) ENDOSCOPIC SYSTEM

(71) Applicant: Karl Storz SE & Co. KG, Tuttlingen (DE)

(72) Inventors: Robert Ayrenschmalz, Niederaichbach (DE); Viktor Josef Wimmer, Seeon (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 875 days.

(21) Appl. No.: 14/488,898

(22) Filed: Sep. 17, 2014

(65) Prior Publication Data

US 2015/0080649 A1   Mar. 19, 2015

(30) Foreign Application Priority Data

Sep. 17, 2013   (DE) .................... 10 2013 110 227

(51) Int. Cl.
| | | |
|---|---|---|
| *A61B 1/00* | (2006.01) | |
| *A61B 1/005* | (2006.01) | |
| *A61B 1/018* | (2006.01) | |
| *A61B 1/31* | (2006.01) | |

(52) U.S. Cl.
CPC ........ *A61B 1/00147* (2013.01); *A61B 1/0016* (2013.01); *A61B 1/0052* (2013.01); *A61B 1/018* (2013.01); *A61B 1/31* (2013.01); *A61B 1/00151* (2013.01)

(58) Field of Classification Search
CPC ............ A61B 1/00006; A61B 1/00105; A61B 1/00142; A61B 1/00147; A61B 1/00151; A61B 1/0016
See application file for complete search history.

(56) References Cited

U.S. PATENT DOCUMENTS

| | | | |
|---|---|---|---|
| 6,554,766 B2 | 4/2003 | Maeda et al. | |
| 6,569,084 B1 | 5/2003 | Mizuno et al. | |
| 6,805,664 B2 | 10/2004 | Doyle et al. | |
| 2003/0018237 A1 | 1/2003 | Okada | |
| 2005/0234293 A1* | 10/2005 | Yamamoto ......... | A61B 1/00147 600/102 |
| 2007/0045504 A1 | 3/2007 | Wollschlaeger | |
| 2007/0135679 A1 | 6/2007 | Hunt et al. | |
| 2011/0208000 A1* | 8/2011 | Honda ............... | A61B 1/00016 600/118 |
| 2012/0071857 A1* | 3/2012 | Goldfarb ................ | A61B 17/24 604/514 |
| 2012/0232476 A1 | 9/2012 | Bhat et al. | |

FOREIGN PATENT DOCUMENTS

| | | |
|---|---|---|
| DE | 102007050226 A1 | 4/2009 |
| EP | 1859724 A1 | 11/2007 |
| EP | 1987789 A1 | 11/2008 |
| EP | 2332459 A1 | 6/2011 |

* cited by examiner

*Primary Examiner* — Timothy J Neal
*Assistant Examiner* — Aaron B Fairchild
(74) *Attorney, Agent, or Firm* — Whitmyer IP Group LLC

(57) ABSTRACT

An endoscopic system according to the invention, in particular for colonoscopy, includes a flexible endoscope with an elongate, flexible shaft, a regulator part, and also an operating part which can be placed on or pushed onto the shaft and which has at least one control element, wherein the endoscopic system furthermore includes a shaft stop, which can be secured on a patient support and which has a locking mechanism, controllable by the at least one control element, for locking the shaft against movement in a longitudinal direction of the shaft.

16 Claims, 6 Drawing Sheets

ENDOSCOPIC SYSTEM

FIELD OF THE INVENTION

The present invention relates to an endoscopic system, in particular an endoscopic system for colonoscopy.

BACKGROUND OF THE INVENTION

In an endoscopic examination of a cavity inside the body, for example a hollow organ, with the aid of a flexible endoscope, an elongate and flexible insertion shaft of the endoscope is inserted through a natural or artificially created opening of the body into the cavity to be examined inside the body. A lens system for generating an endoscopic image is arranged at the distal end of the insertion shaft. To record and convey the endoscopic image from the distal end area (i.e. remote from the observer) of the insertion shaft to a regulator part, which is arranged in a proximal end area (i.e. near the observer) of the shaft, it is possible, for example, for an ordered bundle of light guide fibers to extend inside the shaft. In this case, an endoscopic camera is usually arranged in or on the regulator part, but the regulator part can also have an eyepiece for visual observation. On the other hand, an electronic imaging device can also be arranged in the distal end area of the insertion shaft, and its signals are transmitted to the regulator part via electrical lines extending inside the shaft. The regulator part has a video connection for connecting to an external device for evaluating, displaying and storing the recorded endoscopic image. Moreover, a light-guiding system can be arranged inside the shaft, such that illumination light, coupled in from an external light source via a connection arranged on the regulator part, can be transported to the distal end of the endoscope, where it is used to illuminate the cavity.

It is often necessary to be able to angle the distal end of the shaft in order to make it easier to insert the endoscope through a non-rectilinear channel, to be able to move the tip of the endoscope shaft in a lateral direction inside the cavity, and to be able to change the viewing direction of the lens system arranged in the endoscope tip. For this purpose, the insertion shaft has a controllable portion, in particular a controllable end portion, which can be actively angled in a desired direction and, for this purpose, can be controlled from the direction of the proximal end area of the endoscope. To control the angle of the distal end area of the insertion shaft, suitable operating elements are usually arranged on the regulator part, for example rotary wheels for actuation of wire pulls that extend inside the endoscope shaft and that effect the change of angle. The regulator part is in this case designed as a handpiece which, in addition to the rotary wheels for controlling the deflection of the distal end area of the insertion shaft, comprises further operating elements, such as buttons for operating irrigation and suction valves. The regulator part designed as a handpiece preferably has a supply cable attached to it, which comprises an illumination light guide, a video cable and suction and irrigation lines, and through which these are routed to the corresponding supply devices.

It is also known that the shaft of the flexible endoscope has one or more work channels for the passage of endoscopic work instruments, with which, for example, samples can be collected or surgical manipulations can also be performed inside the cavity. In this case, openings for insertion of the endoscopic work instruments are arranged on the regulator part or in the area of the regulator part.

In an endoscopic examination or operation using a flexible endoscope of this kind, it is often necessary for different movements of the endoscope shaft to be executed alternately or simultaneously. Thus, inserting the insertion shaft into a curved access route not only requires the forward movement of the shaft, it also requires that the distal end area of the insertion shaft is angled in a manner corresponding to the respective curvature of the access route, and, if appropriate, that the insertion shaft is rotated about its longitudinal axis. This applies particularly in the case of an access route that curves several times in different directions, for example the lower and the upper digestive tract. This not only necessitates the angle of the distal end area of the insertion shaft being changed several times and the shaft being rotated several times about its longitudinal axis, it also means that the forward movement occasionally has to be interrupted and the shaft pulled back a short distance in order to obtain an optimal passage through the curving digestive tract and to avoid excessive loading of the walls of the intestine. A forward movement of this kind requires a considerable amount of practice on the part of the operator and, despite this, is often painful for the patient and associated with risks.

EP 1 987 789 A1 discloses an endoscope system comprising a flexible endoscope with an elongate insertion part, and a medical work instrument with a treatment part arranged in a distal area, and a long shaft which is inserted into a channel in the insertion part. The endoscope system further comprises a surgical operating apparatus for entering commands for operating the medical work instrument, a first drive apparatus for driving the treatment part, and a second drive apparatus, which moves the shaft of the medical work instrument to and fro. The surgical operating apparatus comprises an operating lever, with which the motor drives of the medical work instrument can be actuated. For this purpose, the surgical operating apparatus is pushed over the shaft of the endoscope. After the motor drives for actuating the treatment part and for moving the instrument to and fro have been fitted on the endoscope, the shaft of the endoscope is inserted into a cavity inside the body of a patient. In order to collect a tissue sample from the body cavity, the surgeon, by actuating the operating lever, is able to open and close a tissue-removing part of the medical work instrument.

U.S. Pat. No. 6,554,766 B2 discloses an endoscope device which comprises an insertion part with a curvable portion, electric drives for curving the curvable portion, an operation unit for controlling the electric drives, an attachment line for attachment to an external supply unit, a coupling part, and a holding part for holding a holding unit on an operation bed. The operation unit can be fixed on the insertion part and can be held together with the latter in one hand by the surgeon. The operation unit has a convex operating area for controlling the curvable portion of the insertion part, which operating area can be operated by the thumb of the surgeon's hand, and operation switches that can be operated by other fingers. The endoscope can be secured on the operation bed via the holding unit and the holding part. Holding devices for holding a proximal end area of a flexible endoscope are known also from EP 1 859 724 A1 and from U.S. Pat. No. 6,569,084 B1.

To make the insertion of a colonoscopy device easier, US 2007/0135679 A1 proposes fitting a stabilizer in the anus of the patient. The stabilizer has an opening through which the colonoscopy device can be inserted, and a lever for blocking the colonoscopy device relative to the stabilizer.

SUMMARY OF THE INVENTION

The object of the present invention is to make available an endoscopic system of the type mentioned at the outset, which permits easier operation, in particular simpler and safer insertion of the shaft through a curved access route into a cavity inside the body or into a curved hollow organ, and which also permits improved operation when performing an endoscopic procedure.

This object is achieved by an endoscopic system according to the invention.

An endoscopic system according to the invention comprises a flexible endoscope with an elongate, flexible shaft and a regulator part. The elongate, flexible shaft is designed for insertion into a cavity inside the body, for example into a hollow organ, by way of a natural or artificially created opening of the body. The shaft is suitable in particular for insertion into the digestive tract in a colonoscopy procedure. The shaft, also referred to hereinbelow as insertion shaft, has, at its distal end, a lens system for generating an endoscopic image of the cavity inside the body, and has, in its interior, means for conveying the endoscopic image from the distal end area to the proximal end area. The regulator part arranged at the proximal end of the shaft can have connections for supplying the endoscope and for conveying the endoscopic image to an image processing, displaying and/or storing device. Moreover, the regulator part can have drives for adjusting the angle of the distal end area of the insertion shaft, and couplings for such drives. The insertion shaft can also have irrigation and suction lines, and also work channels for endoscopic work instruments, for which corresponding connections or admission openings can be arranged on the regulator part.

The endoscopic system further comprises an operating part, which can be placed laterally on or pushed onto the shaft. Thus, the operating part is in particular configured in such a way that it can be placed on the shaft or can be pushed onto the shaft via the distal end thereof and, for example, can be held together with the shaft in one hand by the operator. The operating part has at least one control element.

According to the invention, the endoscopic system further comprises a shaft stop, which can be secured on a patient support and which has a locking mechanism, controllable by the at least one control element, for locking the shaft against a movement in a longitudinal direction of the shaft. The patient support can be, for example, a couch or an examining or operating table, on which the patient lies during an examination performed with the endoscopic system. However, in the present context, a patient support is also understood as a chair, for example, or another device which supports the patient during the examination or operation, or with respect to which the opening in the body, through which the flexible shaft is inserted, lies in a fixed spatial relationship. The shaft stop can also, for example, be connected to the patient support via a medical retaining arm. The shaft stop is configured in such a way that the shaft of the endoscope can be inserted into it or placed on it, such that the locking mechanism can act on the shaft. The locking mechanism can, for example, be configured as a clamp mechanism in which one or more clamp elements, for example a pressure plate and a counter-pressure plate between which the shaft of the endoscope can be placed, can be controlled by the control element and are adjustable by motor for clamping the shaft. In particular, all parts of the locking mechanism are accommodated in the shaft stop. Advantageously, therefore, no devices are needed on the endoscope shaft in order to fix the shaft to the shaft stop. The shaft stop can therefore be used with any conventional endoscope.

When the locking mechanism is activated by suitable control from the control element, the shaft is blocked against movement in the longitudinal direction, in which case a certain degree of mobility in a transverse direction of the shaft can be allowed or can likewise be blocked. In an operational state of the endoscopic system, the locking mechanism is thus controlled by the control element to lock or release the shaft in respect of a movement in the longitudinal direction. A rotation of the shaft about its longitudinal axis is possible in the released state of the shaft, and it can still be possible, or can likewise be blocked, in the state when locked by the locking mechanism. In an assembly state of the endoscopic system, the shaft, for insertion into the shaft stop, can be movable at all times in the longitudinal direction, independently of the control element, and also rotatable about its longitudinal axis. The operating part can be placed on the shaft in the proximal direction from the shaft stop, or, before the shaft has been inserted into the shaft stop or into the locking mechanism or has been placed thereon, the operating part can be pushed onto the shaft via the distal end thereof.

By virtue of the fact that the shaft can be fixed in its longitudinal direction by the locking mechanism of the shaft stop that can be secured on the patient support, it is possible, in an endoscopic procedure, to fix an attained insertion position of the shaft in a hollow organ inside the body. In this way, the operator does not need to actively hold the shaft in this position, and, independently of maintaining the longitudinal position, is able to take further measures, for example rotating the shaft about its longitudinal axis or adjusting the angle of the distal end in order to overcome a subsequent curvature of the hollow organ during further insertion of the shaft. Similarly, without having to actively hold the shaft in the attained longitudinal position, the operator is able to perform surgical manipulations with the aid of work instruments that are guided through the shaft. Moreover, by virtue of the fact that the operating part can be placed on or pushed onto the shaft, the forward movement, rearward movement and rotation of the shaft are made easier, especially if the operating part, when placed laterally on the shaft or pushed onto the latter, can be gripped together with the shaft in one hand and can be moved to and fro, together with the shaft, in the longitudinal direction or rotated about the longitudinal axis of the shaft. Finally, the operation of the endoscopic system is further facilitated by the fact that the operating part has the control element for locking or releasing the shaft in respect of a movement in the longitudinal direction, since the operating part with the control element can be moved together with the shaft in the longitudinal direction. This greatly facilitates the work of the surgeon and reduces the associated risk.

According to a preferred embodiment of the invention, the operating part has a recess in the shape of a half-shell for receiving the shaft. When the operating part is placed on the shaft, the shaft is thus received in the half-shell, such that the operating part laterally encloses the shaft at least partially. This has the effect that the operating part can be placed laterally on the shaft, and the shaft can be held securely on the operating part and, in addition, is guided in the longitudinal direction. Particularly preferably, the operating part with the half-shell is configured in such a way that the operating part can be gripped in one hand together with the shaft inserted into the half-shell and, at the same time, the shaft can be pressed firmly into the half-shell, such that there is a sufficient frictional engagement between the hand of the operator, the shaft and the operating part in order to move the shaft in its longitudinal direction and/or to rotate it about its longitudinal axis. This is a particularly simple way of allowing the operator to manipulate the shaft with just one hand.

Additionally or alternatively to the half-shell-shaped recess, a surround element can be provided with which the operating part can be secured on the shaft firmly, in particular sufficiently firmly in the longitudinal direction, to bring about a longitudinal movement of the shaft and/or a rotation of the shaft about its longitudinal axis. In this case, the operating part can enclose the shaft. In this way too, a particularly simple and safe manipulation of the insertion shaft is permitted with just one hand.

According to a preferred embodiment of the invention, provision is made that, if the operating part has only a single control element, this is configured as a shaft sensor for detecting the placement of the shaft on the operating part; if the operating part has several control elements, at least one of the control elements is configured in this way. The locking mechanism can be controlled by the shaft sensor in such a way that, when the operating part is not placed on or pushed onto the shaft, the shaft is locked. This means that, in an operational state of the endoscopic system, the shaft can be released, for movement in the longitudinal direction relative to the shaft stop, only when the operating part is placed on or pushed onto the shaft. A possible release of the shaft from the shaft stop thus takes place on the basis of a signal from the shaft sensor, which signal indicates whether the shaft bears on the operating part. It is thus possible to ensure that, in an operational state of the system, a longitudinal movement of the shaft is always ruled out whenever the operating part is not connected to the shaft, in which case it can be concluded that an operator has not gripped the shaft in order to hold or move it.

The shaft sensor is preferably configured as a pressure sensor. In particular, the pressure sensor is arranged on an inner surface of the half-shell. In this way, it is not only possible to detect particularly reliably whether the shaft bears on the operating part, but also whether the operating part and the shaft are pressed firmly onto each other by an operator. This means that the shaft can be released, for movement in the longitudinal direction relative to the shaft stop, only when the shaft and the operating part have been gripped by an operator with a force sufficient to control the longitudinal movement of the shaft. In this way, it is possible in particular to avoid a situation in which the shaft is released for longitudinal movement at a time when the operator does not have sufficient control over the shaft.

According to another preferred embodiment of the invention, provision is made that, if the operating part has only a single control element, the latter is configured as an operating element for manually controlling the locking mechanism. If the operating part has several control elements, at least one of the control elements is configured in this way, it being possible, for example, for another control element to be configured as a shaft sensor. An operating element for manually controlling the locking mechanism can be configured, for example, as a pushbutton or as an operating lever (joystick) and can advantageously be arranged on the operating part in such a way that it can be actuated by a finger of the same hand in which an operator is holding the operating part together with the shaft. This is a simple way of permitting manual operation of the locking mechanism in order to facilitate the use of the endoscopic system.

Advantageously, the operating part has at least two control elements, namely at least one shaft sensor, which can be configured for example as a pressure sensor arranged in a half-shell provided for receiving the shaft, and also at least one operating element for manually controlling the locking mechanism. The at least one shaft sensor and the at least one operating element are in this case connected in such a way that the locking mechanism can be controlled by the operating element only when the signal of the shaft sensor indicates the presence of the shaft on the operating part. In the operational state of the endoscopic system, this means that, whenever the signal of the shaft sensor indicates that the operating part is not placed on or pushed onto the shaft, the locking mechanism blocks the shaft in respect of a longitudinal movement, and it does so independently of an actuation of the at least one operating element. On the other hand, in the operational state when, according to the signal of the shaft sensor the operating part is placed on or pushed onto the shaft, the at least one operating element is active, i.e. the locking mechanism can be controlled by the latter, and the shaft can be alternately locked or released. In an assembly state of the endoscopic system, a movement of the shaft in its longitudinal direction may be possible independently of the shaft bearing on the operating part. Since the operating part has both a shaft sensor and also an operating element for controlling the locking mechanism, and since the operating element permits control of the locking mechanism only when a signal of the shaft sensor indicates the presence of the shaft on the operating part, this permits particularly reliable and comfortable operation of the endoscopic system. In particular, there is an automatic fixing of the shaft in or on the shaft stop when the operating part is not placed on or pushed onto the shaft, and it can thus be concluded that the operator is not ready to execute a longitudinal movement of the shaft. On the other hand, complete manual control of the longitudinal movement of the shaft is permitted when the shaft bears on the operating part and when in particular it can be concluded, from the signal of a shaft sensor designed as pressure sensor, that the operator is gripping the operating part and the shaft with sufficient force.

Preferably, the operating part comprises one or more operating elements for controlling further functions of the endoscopic system. According to a particularly preferred embodiment of the invention, the operating part has an operating element, for example a toggle switch, a joystick or a touchscreen, for controlling the angle of the distal end portion of the shaft. For example, the operating part can also have, as operating element, a menu control which allows several or even all of the functions of the endoscope to be operated with one hand. Preferably, the operating element is arranged, or the operating elements are arranged, in such a way as to permit actuation by the same hand with which an operator is holding the operating part and the shaft. The operation of the endoscopic system is further facilitated in this way.

Advantageously, a further operating part can be provided which, in particular, can have operating elements for controlling one or more endoscopic work instruments that can be guided through the shaft of the endoscope to the cavity inside the body. The functions of the endoscopic work instruments that are to be controlled include, in particular, a longitudinal movement in the direction of the insertion shaft and the actuation of a tool, for example forceps, scissors or a sling, arranged at the distal end of an endoscopic work instrument, which tool can be used for carrying out manipulations in the cavity inside the body, for example for removing a tissue sample or for performing an endoscopic surgical procedure. For this purpose, suitably configured motor drives of the endoscopic work instruments can be provided. By virtue of the fact that a further operating part is present that can be gripped by the user in his second hand, simple and complete operation of the endoscopic system by a single user is permitted. The further operating part can also be configured as a menu control, which can alternately be placed on the first-mentioned operating part or can be operated separately from the latter.

Alternatively, it is also advantageously possible to provide a single operating part which is configured both as described above, for controlling the functions of the endoscopic system, and also for controlling the stated functions of one or more endoscopic work instruments.

To control the locking mechanism, the control element can be connected to the locking mechanism directly by an electrical line or indirectly via a control device of the endoscopic system. Advantageously, the locking mechanism can be controlled by the control element via a wireless connection. Such a wireless connection can be provided, for example, by a wireless connection between the operating part and a control device and a wireless or wired connection between the control device and the locking mechanism, or also by a wired connection between the operating part and the control device and a wireless connection between the control device and the locking mechanism. A further operating part can also be connected wirelessly to the control device. This permits a simple and reliable structure and a particularly comfortable operation of the endoscopic system.

According to a preferred embodiment of the invention, the shaft stop has a through-opening which is designed to hold the shaft in a transverse direction of the shaft. Upon assembly of the system, the shaft is guided through the through-opening, or the shaft is placed into a recess of the shaft stop and held in said recess by a closure piece, for example by a bow or an elastic element, the through-opening being formed by the recess together with the closure piece. The through-opening can be configured to allow different directions of the shaft, or the shaft stop can have a guide through which the shaft is guided in a predefined direction. The through-opening can also be formed, for example, by a retainer bushing which is pivotable within a limited angle range and through which the shaft can be guided. A rotation of the shaft about its longitudinal axis is preferably still possible. This further improves the handling of the endoscopic system. In particular, this means that, in an area between the shaft stop and the body opening through which the shaft is inserted, the insertion shaft is held or guided in such a way that deflection or buckling of the shaft can be reliably avoided even in the event of a pushing movement for moving the shaft forward.

It is furthermore preferred that the shaft stop, in the distal direction from the locking mechanism or in the distal direction from the through-opening, has a tube holder for holding a tubular shaft protection film, it also being possible for a retainer bushing, through which the shaft can be guided, to be configured as a tube holder. The shaft protection film can be pulled over the insertion shaft in such a way that it can be secured with a proximal end on the proximal end area of the insertion shaft, and a distal end of the shaft protection film is carried by the tube holder. The area between the regulator part and the shaft stop is thus surrounded by the shaft protection film; the operating part can be placed on the shaft surrounded by the shaft protection film. When the shaft is pushed forward or pulled back, that portion of the insertion shaft located in the proximal direction from the shaft stop is surrounded by the shaft protection film; the part of the shaft located inside the shaft stop is likewise surrounded by said film. Therefore, when the insertion shaft is pulled out of the cavity inside the body, any contamination of the insertion shaft cannot affect the shaft stop and the operating part, nor does it lead to contamination of the associated areas of the patient support. The shaft stop with the tube holder can be arranged close enough to the body opening through which the shaft is inserted to ensure that the exposed area of the shaft extending between the body opening and the tube holder of the shaft stop does not come into contact with the patient support, with the result that contamination can be avoided in this respect too. When the insertion shaft has been pulled completely out of the body opening, the shaft protection film, for this purpose expediently having a surplus length in relation to the length of the insertion shaft, can be pulled over the distal end of the shaft, such that the insertion shaft is completely enveloped and can be transported for cleaning and decontamination.

According to a particularly preferred embodiment of the invention, the regulator part comprises supply connections and/or drive couplings of the endoscope and can be attached to a supply device, which can likewise be part of the endoscopic system. The supply connections are in particular connections for transmitting the illumination light and for feeding electrical power to the endoscope, and also connections for transmitting a video signal to an image processing, displaying and storing device, and connections for introducing a flushing liquid into an irrigation channel of the endoscope and for aspiration thereof from a suction channel of the endoscope. The regulator part can have drive couplings for connection of drives or transmission means for adjusting the angle of the distal end area of the insertion shaft, for example wire pulls, with motor drives that are assigned to the supply device. The supply device can furthermore have motor drives for endoscopic work instruments, which can likewise be attached to corresponding couplings of the work instruments or of the regulator part. In particular, the regulator part can have a closed housing which, on its outside, carries the supply connections and drive couplings. This permits supply to the endoscope and a simple design, since the endoscope itself does not need to have any motor drives.

Preferably, the shaft is connected to the regulator part, or to the housing of the regulator part, so as to be rotatable. In this way, it is possible to rotate the insertion shaft in a direction suitable for insertion through a curved access route or into a curved hollow organ, so as to be able to adopt an optimal angle of the distal end portion. This also makes it possible to choose an optimal orientation of the lens system or of the tools of the endoscopic work instruments. To make rotation of the shaft easier about its longitudinal axis, a rotary handle or a rotary lever protruding laterally from the shaft can be arranged adjacent to the regulator part. Preferably, the rotation of the shaft relative to the regulator part is limited to a restricted angle range, for example a maximum of ±180°, in order to avoid excessive twisting of the lines that are routed inside the shaft and the regulator part. Moreover, the shaft can be connected to the regulator part or to the housing of the regulator part releasably, so as to simplify the cleaning and/or sterilization of the shaft.

It will be appreciated that the aforementioned features, and the features still to be explained below, can be used not only in the respectively cited combination but also in other combinations or singly, without departing from the scope of the present invention.

BRIEF DESCRIPTION OF THE DRAWINGS

Further aspects of the invention will become clear from the following description of a preferred illustrative embodiment and from the attached drawing, in which.

DETAILED DESCRIPTION OF THE INVENTION

Figure 1:
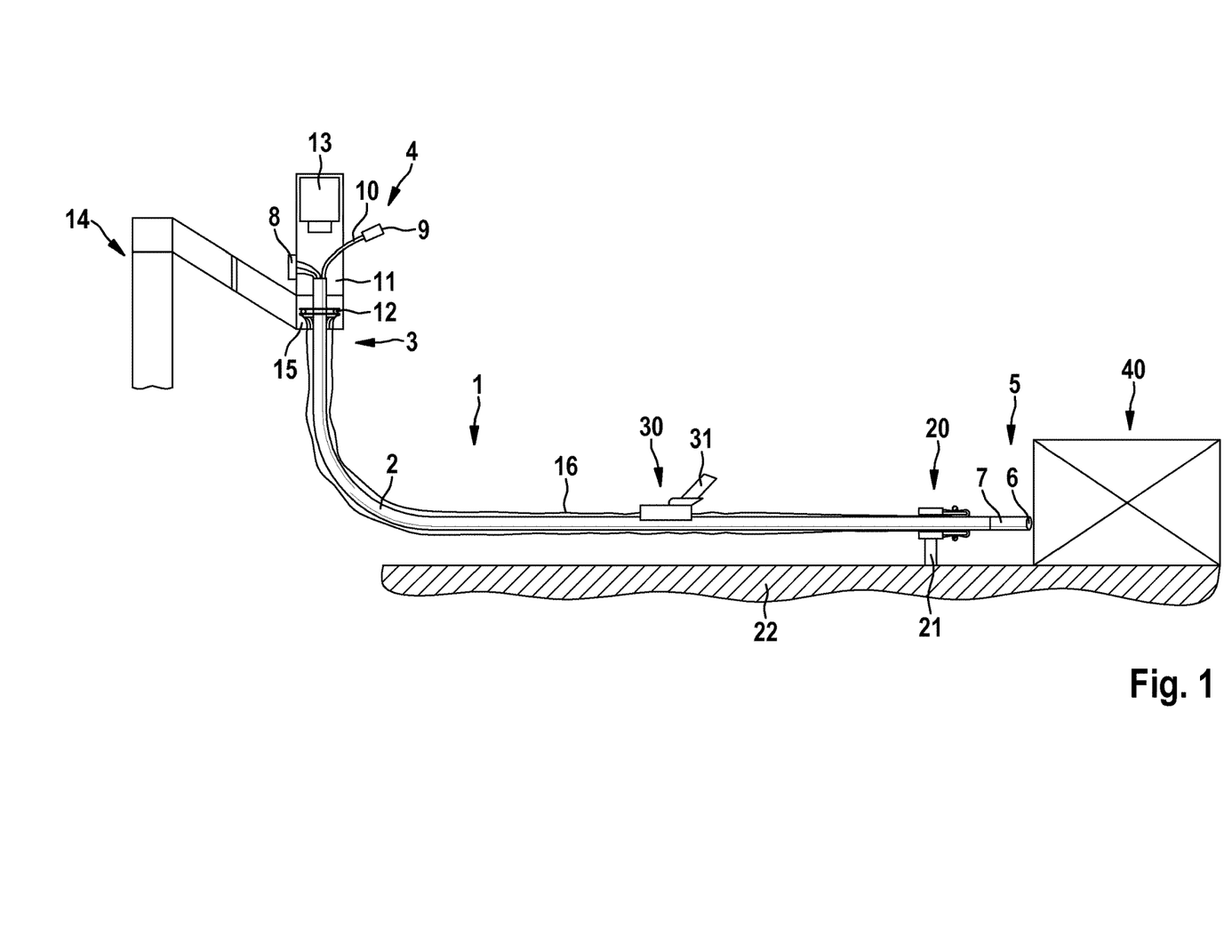
FIG. 1 shows an illustrative embodiment of an endoscopic system according to the invention in a general view.

As is shown schematically in a general view in FIG. 1, an endoscopic system according to the invention in a first illustrative embodiment comprises a flexible endoscope 1 with an elongate, flexible shaft 2 and, attached to the proximal end 3 of the shaft 2, a regulator part which is designed as an endoscope box 4. At the distal end 5 of the insertion shaft 2, an endoscope lens 6 is provided for generating an endoscopic image that is taken, for example, by an electronic imager and is transmitted to the endoscope box 4 via electrical lines running inside the shaft 2. The distal end area 7 of the shaft 2 is designed to be maneuverable and, by way of wire pulls extending inside the shaft 2, can be angled in one or more directions transversely with respect to the longitudinal axis of the distal end portion 7.

The shaft 2 further comprises light guides, by which illumination light coupled in at the endoscope box 4 is conveyed to the distal end 5, and suction and irrigation channels for guiding air or liquid to the distal end 5 and aspirating it from there again, and a work channel through which an endoscopic work instrument is passed through the shaft 2 to the distal end 5 of the latter. The endoscope box 4 has a connection 8 for a video cable for attachment to an external video unit, and connections (not shown in FIG. 1) for a light cable for attachment of an external light source, and irrigation and suction connections. Moreover, in the area of the endoscope box 4, an opening 9 of the work channel is situated on an angled work channel guide 10, into which the endoscopic work instrument can be pushed. The video connection and the other connections (not shown) for the illumination light and for the suction and irrigation lines are arranged on the outside of a housing 11 on which the shaft 2 is secured rotatably via a rotary bearing 12. To avoid excessive twisting of the cables, lines and channels extending through the rotary bearing 12, the rotation of the shaft 2 about its longitudinal axis on the rotary bearing 12 is limited to an angle range of ca. ±180° C. by abutments (not shown in FIG. 1). To control the angle of the distal end portion 7 of the shaft 2, a motor drive 13, shown symbolically in FIG. 1, can likewise be accommodated inside the housing 11 of the endoscope box 4. However, according to a variant not shown in FIG. 1, couplings can also be provided for transferring a drive movement from an external motor drive. The housing 11 can contain further components, for example a processor and the illumination light source. According to the variant shown in FIG. 1, the endoscope box 4 is held by a retaining arm 14, which engages on a connecting portion 15 of the endoscope box 4, which connecting portion 15 also has the rotary bearing 12 for holding the proximal end 3 of the shaft 24. The total length of the shaft 2 is, for example, about 150 cm or more in the case of a system suitable for colonoscopy.

The endoscopic system further comprises a shaft stop 20, which is shown only symbolically in FIG. 1 and which can be secured on a patient support 22 via a resilient mount 21. The endoscopic system further comprises an operating part 30, which can be held in one hand by an operator and can be placed onto the shaft 2, and onto which operating part 30 a menu control 31 having further operating elements can be fitted, as shown in FIG. 1. The shaft stop 20 and the operating part 30 are explained in more detail below.

As is shown in FIG. 1, in order to perform an endoscopic examination or operation, the shaft stop 20 is arranged at a suitable distance, for example ca. 15-20 cm, from a patient 40 and is secured on the patient support 22 on which the patient to be examined or operated on is lying. The body opening through which the shaft 2 of the endoscope 1 is to be inserted into a cavity inside the body of the patient, in order to perform the planned intervention, is directed toward the shaft stop 20, and the mount 21 is configured in such a way that the shaft 2 guided through the shaft stop 20 can be inserted substantially in a straight line into the cavity inside the body. The endoscopic system shown in FIG. 1 is configured in particular for performing a colonoscopy procedure.

The shaft 2 is placed into the shaft stop 20 or is guided with its distal end portion 7 through the shaft stop 20. The operating part 30 is placed onto the shaft 2 in the proximal direction from the shaft stop 20, with a distance remaining between the shaft stop 20 and the operating part 30. The distance is chosen such that the shaft 2 can be pushed forward together with the operating part 30 without the shaft deflecting or buckling between the operating part 30 and the shaft stop 20. The operating part 30 has a shaft sensor (explained in more detail below) which is coupled to a locking mechanism of the shaft stop 20 in such a way that the shaft 2 inside the shaft stop 20 is movable in the longitudinal direction, i.e. for insertion into or withdrawal from the cavity inside the body of the patient 40, only when the operating part 30 is placed onto the shaft 2 and is pressed firmly thereon. The endoscope box 4 is held in such a way that the shaft 2 of the endoscope 1 can be pushed into the cavity inside the body, for which purpose a curvature, comprising a sufficient length of the shaft, can be provided in the area between the operating part 30 and the endoscope box 4, or, for example, the endoscope box 4 can be moved with the retaining arm 14 closer to the patient. In this state, the shaft 2 can be moved toward the patient 40 or away from the patient 40 in the longitudinal direction; otherwise, the shaft 2 is blocked in the shaft stop 20.

The shaft 2 of the endoscope 1 is surrounded by a tubular shaft protection film 16, of which the proximal end is secured on the proximal end 3 of the shaft 2, for example by adhesive bonding or with the aid of an adhesive tape. At the distal end, the shaft protection film 16 is held on the shaft stop 20 and, for this purpose, can have a suitable reinforcement. On its inner face, and optionally on its outer face, the shaft protection film 16 has a sliding lining in order to allow the shaft 2 surrounded by it to move more easily inside the shaft stop 20. During a movement of the shaft 2, the shaft protection film 16 does not move, or moves only slightly, inside the shaft stop 20. Instead, in the proximal direction from the shaft stop 20, the shaft protection film 16 is gathered during the forward movement of the insertion shaft 2 and is smoothed out when the insertion shaft 2 is pulled back.

Figure 2A:
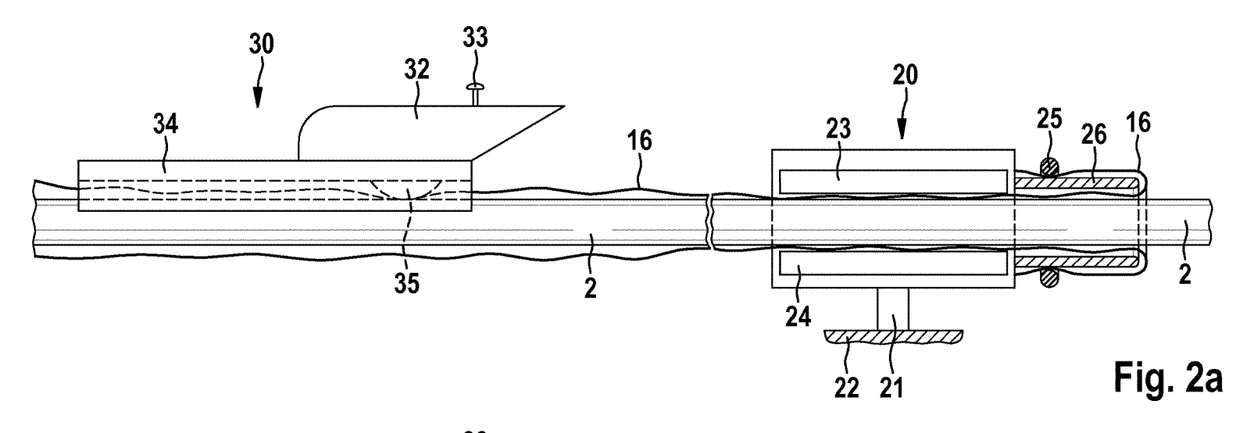
FIGS. 2a and 2b show two partially cutaway side views of the shaft stop and of the operating part according to an illustrative embodiment of the invention in two operational states.

In a first embodiment of the shaft stop 20, as is shown in FIG. 2a, a first portion of the shaft 2 is guided through the shaft stop 20, which is secured on the patient support 22 by the mount 21. The shaft stop 20 comprises a locking mechanism, which is formed by a movable pressure plate 23 and a stationary counter-pressure plate 24, wherein the movable pressure plate 23 can be moved toward and away from the counter-pressure plate 24 by motor. The pressure plate 23 and the counter-pressure plate 24 can be provided with a friction-enhancing surface and with a padding for increasing the friction with the shaft portion inserted between them and for avoiding damage to the shaft. To make it easier to insert the shaft 20 between the pressure plate 23 and the counter-pressure plate 24, the pressure plate 23 for example can be secured on a pivotable retainer (not shown). The shaft stop 20 furthermore has a flexible bow 25 forming a through-opening through which the shaft 2 is guided. Arranged at the distal end of the shaft stop 20 is a tube holder 26, across which the shaft protection film 16 is pulled. The shaft protection film 16 is likewise held on the shaft stop 20 by the bow 25, it being possible for the shaft protection film to be provided with a reserve length (not shown in FIGS. 2a and 2b).

To lock the shaft 2 against a movement in its longitudinal direction, the movable pressure plate 23 is moved by motor in the direction of the counter-pressure plate 24, and the shaft 2 is thus clamped between the pressure plate 23 and the counter-pressure plate 24 and thereby blocked. A certain amount of lateral movement and pivoting of the shaft can moreover be permitted by a resilient configuration of the mount 21.

Figure 2B:
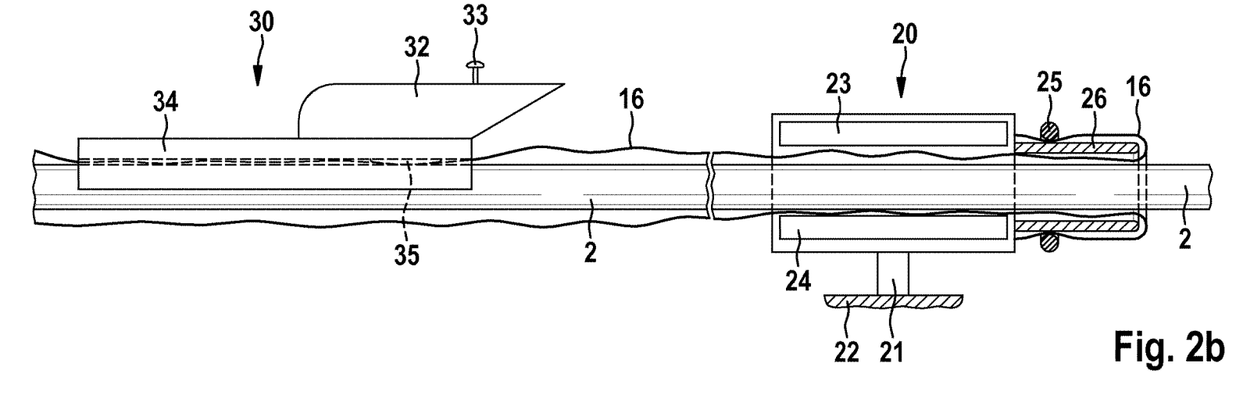

The operating part 30 according to FIGS. 2a and 2b comprises a carrier 32, which carries a joystick 33. A half-shell 34, which is shaped to receive the shaft 2, is arranged on the underside of the carrier 32. On the inside of the half-shell 34 there is a pressure sensor 35, which can be actuated by firm pressing on the shaft 2. The operating part, together with the portion of the shaft 2 placed in the half-shell 34, can be gripped in one hand by the operator, and the shaft 2 can thus be pressed into the half-shell 34 such that the pressure sensor 35 is actuated. While holding the shaft 2 on the operating part 30, the operator can at the same time actuate the joystick 33 with one finger.

In the situation shown in FIG. 2a, the shaft 2 is not applied firmly to the operating part 30. The pressure sensor 35 does not therefore emit a signal indicating the presence of the shaft 2. The pressure sensor 35 is connected by a wireless connection to a control device (not shown) which controls the locking mechanism of the shaft stop 20. The control device is configured in such a way that, when no signal indicating the presence of the shaft 2 is received from the pressure sensor, the locking mechanism is at all times closed, i.e. the pressure plate 23 is controlled to clamp the shaft 2 against the counter-pressure plate 24.

In the situation shown in FIG. 2b, the shaft 2 is placed into the half-shell 34 and is pressed firmly onto the latter, such that the pressure sensor 35 generates a signal indicating the presence of the shaft 2. In this case, the pressure plate 23 is moved in the opposite direction by the control device and is thereby released from the shaft 2, such that the latter can move freely in the longitudinal direction together with the shaft protection film 16.

Figure 3A:
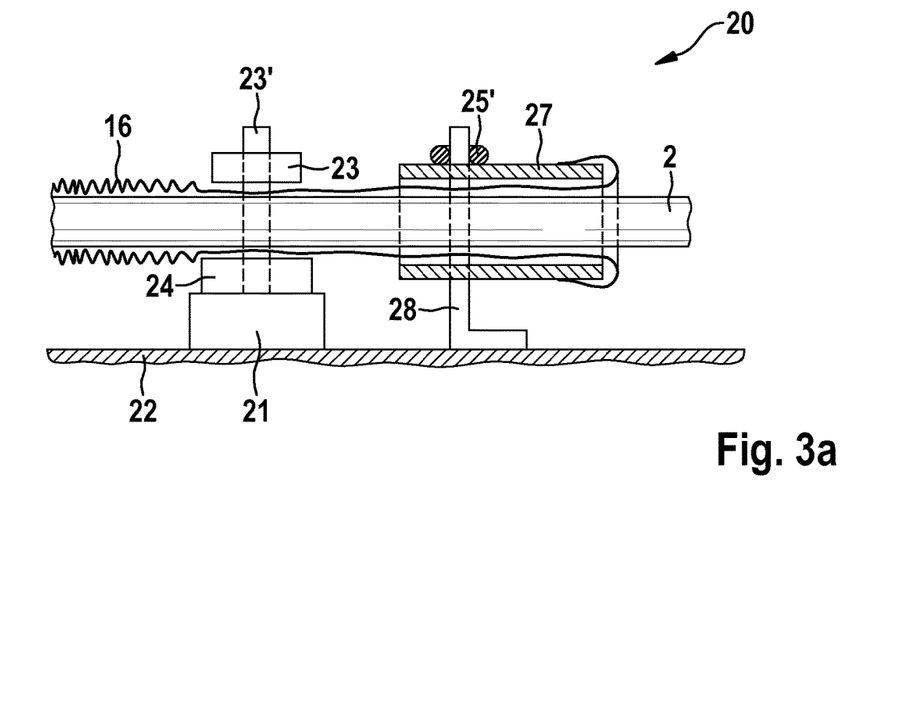
FIGS. 3a and 3b show an alternative embodiment of the shaft stop in a partially cutaway side view (FIG. 3a) and a plan view (FIG. 3b)
Figure 3B:
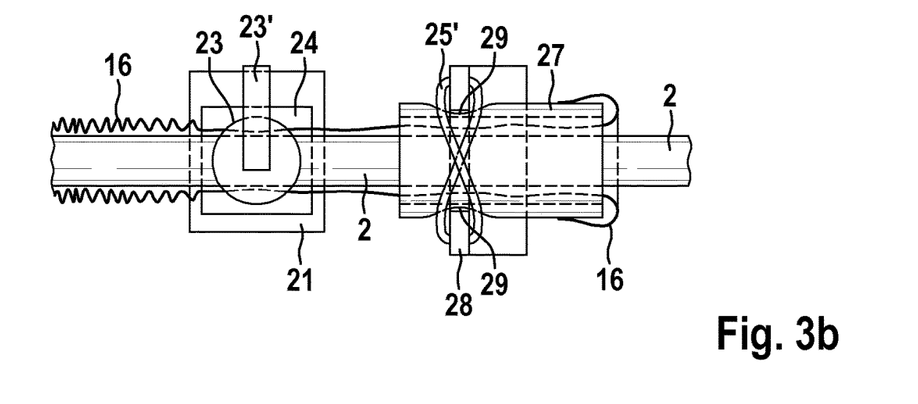

In the second embodiment of the shaft stop shown in two views in FIGS. 3a and 3b, the shaft stop comprises a locking mechanism, which is secured on the patient support 22 with the mount 21, and a shaft guide which is separate from the locking mechanism and, for example, is movable relative to the latter on a rail. The locking mechanism is formed by a movable pressure plate 23 and a stationary counter-pressure plate 24, wherein the movable pressure plate 23 can be moved toward and away from the counter-pressure plate 24 by motor in order to respectively lock and release the shaft 2 in terms of a movement in the longitudinal direction. The pressure plate 23 is secured on a swivel arm 23'. The shaft guide comprises a retainer bushing 27 through which the shaft 2 is guided. The retainer bushing 27 is held by a rubber band 25' in a fork 28, which is secured on the patient support 22. Notches 29 lying opposite each other in the outer face of the retainer bushing 27 allow the retainer bushing 27 to be held with play in the fork 28, thereby permitting a swiveling movement of the retainer bushing 27 within a limited angle range and, therefore, an adjustment of the guide of the shaft 2 in a desired direction. The distal end of the shaft protection film 16 is secured, for example adhesively bonded, on the outside of the retainer bushing 27. At the proximal end, the shaft protection film 16 has a reserve length, which is indicated by the gathering of the shaft protection film 16 in FIGS. 3a and 3b. In other respects, the endoscopic system is configured as shown in FIGS. 1 to 2b.

Figure 4A:
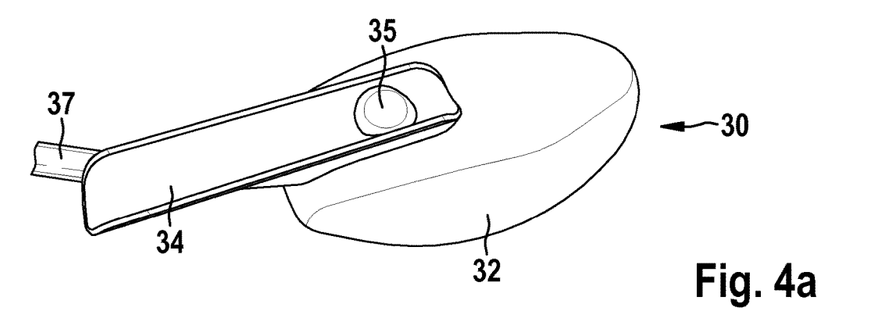
FIGS. 4a and 4b show the operating part from FIGS. 2a and 2b in a perspective view from below and during operation by a hand of an operator.
Figure 4B:
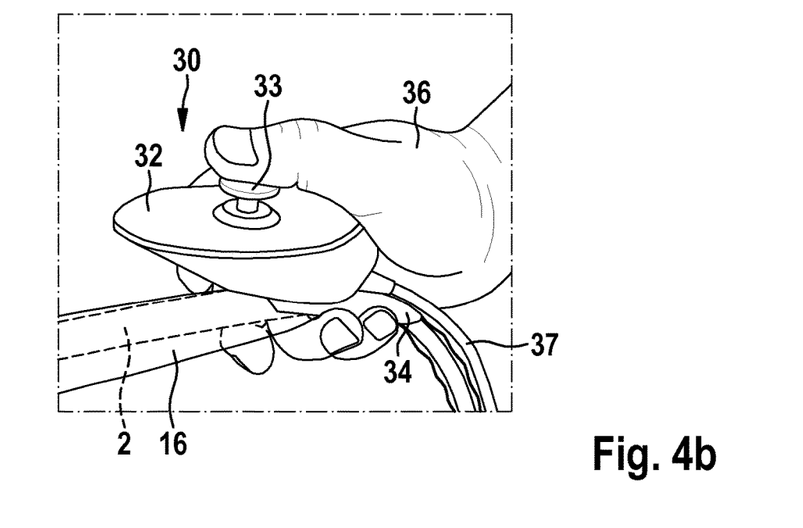

In FIG. 4a, the operating part 30 is shown in a perspective view from underneath. The half-shell 34 is secured on the underside of the carrier 32. A pressure sensor 35 protrudes through a recess of the half-shell 34 into the space formed by the half-shell 34, such that the pressure sensor 35 is actuated when the shaft 2 is firmly applied. As is shown in FIG. 4b, the operator can grip the operating part 30 together with the shaft 2 in one hand 36 and hold them in such a way as to permit both a movement of the shaft 2, together with the operating part 30, in a longitudinal direction and also an actuation of the joystick 33 with one finger of the hand 36. The shaft protection film 16 is thus gripped too. The joystick 33 serves to control the angle of the distal end area of the shaft 2 and for this purpose is connected to the control device (not shown) which controls the angle according to the signal emitted by the joystick 33. In the embodiment shown in FIGS. 4a and 4b, the operating part is connected to the control device via a cable 37. However, variants with wireless signal transmission are also possible.

Figure 5A:
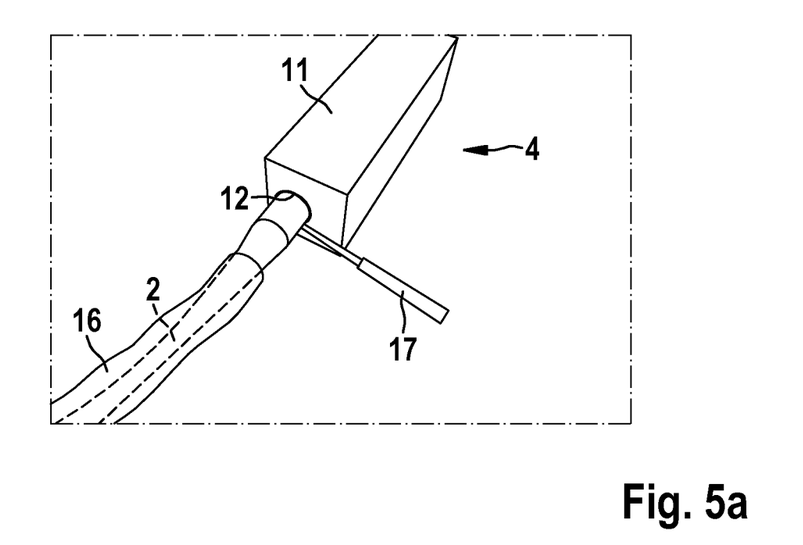
FIGS. 5a and 5b show a regulator part according to a further illustrative embodiment of the endoscopic system in two perspective views.
Figure 5B:
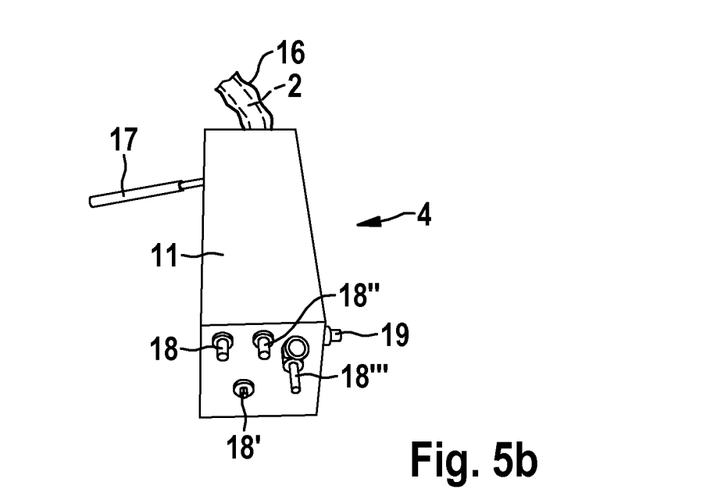

In FIGS. 5a and 5b, the endoscope box 4 is shown in two different perspective views. The shaft 2 is connected rotatably to the housing 11 of the endoscope box 4 via the rotary bearing 12. To make rotation of the shaft easier, a rotary lever 17 is mounted on the shaft 2 in the area of the rotary bearing 12. The shaft protection film 16 is secured to the shaft 2 with the aid of an adhesive tape in front of the rotary bearing 12 and thus follows a rotation of the shaft 2. As is shown in FIG. 5b, connections 18, 18', 18" and 18''' for the irrigation and suction functions are arranged on the proximal end area of the housing 11, and corresponding hoses for attachment to external supply devices can be attached to these connections. For cleaning and sterilization, the housing 11 is leaktight, it being possible for the connections 18, 18', 18", 18''', the coupling 19 described below, and further connections not shown in FIGS. 5a and 5b, to be covered in a leaktight manner by a covering.

Figure 6:
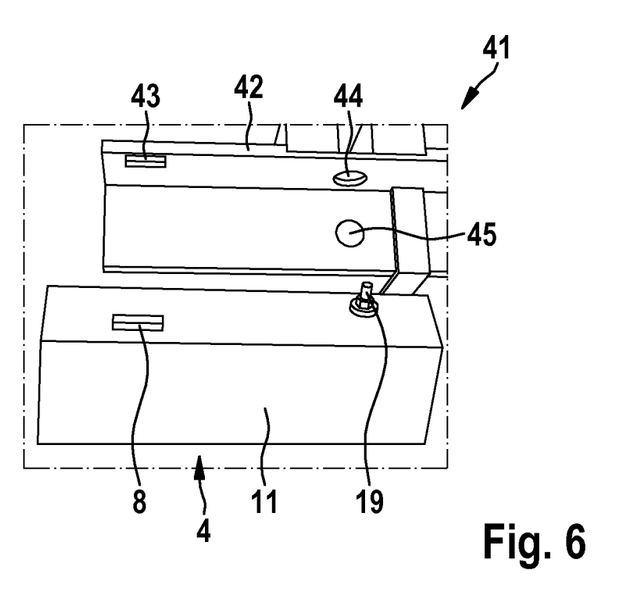
FIG. 6 shows the regulator part from FIGS. 5a and 5b with a supply adapter of a supply device.

As is shown in FIG. 6, a supply adapter 41 of an external supply device is configured in such a way that the housing 11 of the endoscope box 4 can be fitted into an angled seat 42 in such a way that the video connection 8 is connected to a video socket 43, and a coupling 19 cooperates with a coupling connection 44 of the drives for the wire pulls for angling the distal end area of the shaft. FIG. 6 also shows the light outlet 45. For safety reasons, the light is output only when the housing 11 has been inserted into the seat 42.

To assemble the system according to the invention, the shaft stop 20 is secured on the patient support 22 (see FIG. 1). The shaft 2 of the endoscope 1 is covered with the shaft protection film 16 and placed into the shaft stop 20 on the counter-pressure plate 24 and secured in the shaft stop 20 by the bow 25 or pushed through the retainer bushing 27 (see FIGS. 2a and 2b and FIGS. 3a and 3b). The pressure plate 23 is swiveled over the shaft, such that the shaft 2 extends between the pressure plate 23 and the counter-pressure plate 24. In the embodiment shown in FIGS. 2a and 2b, the shaft protection film 16 is secured on the tube holder 26 by the bow 25, as a result of which the shaft 2 itself is also guided. In the embodiment shown in FIGS. 3a and 3b, the shaft 2 is guided with the shaft protection film 16 through the retainer bushing 27, and the shaft protection film 16 is affixed to the retainer bushing 27. In the assembled state of the endoscopic system, the shaft 2 is movable in the longitudinal direction. The endoscope box 4 is inserted with the housing 11 into the seat 42 of the supply adapter 41 of the supply device (see FIG. 6). Alternatively, the endoscope box 4 can also be held by the retaining arm 14 shown in FIG. 1, in which case the connection lines are attached separately. The supply adapter 41 can also be held by a retaining arm.

With the patient 40 now lying on the patient support 22 at a distance of about 15-20 cm from the shaft stop 20, as is shown symbolically in FIG. 1, the system is switched on to produce the operational state. In this state, the shaft is blocked in the shaft stop 20 against movement, as long as the operating part 30 is not placed onto the shaft 2 (see FIG. 2a). It is only when the operator, generally the gastroenterologist performing the endoscopic procedure, places the operating part 30 onto the shaft 2 and presses the latter firmly into the half-shell 34 that the control device, on account of the signal from the pressure sensor 35, controls the movable pressure plate 23 in such a way that the shaft 2 is released and can be moved together with the shaft protection film 16 inside the shaft stop 20 (see FIG. 2b). By means of a pushing movement performed by the hand 36 that grips the operating part 30 together with the shaft 2, the latter can now be inserted into the access opening and through the latter into the cavity inside the body of the patient 40. A rotation movement of the shaft 2 can also be performed in this way, which can additionally be supported by the rotary lever 17 (see FIGS. 5a and 5b). To make insertion easier, the surgeon, by actuating the joystick 33, can control the angle of the distal end portion 7 of the shaft 2 of the endoscope 1 by motor in the manner of a remote control. In addition, the forward movement of the shaft 2 is made easier by the fact that the shaft 2 is guided in the shaft stop 20.

During the endoscopic procedure, a distal portion of the shaft 2 is located inside the endoscopic access route and the cavity inside the body of the patient 40. When the procedure is being performed, the shaft 2 can be moved to and fro by the surgeon pressing the shaft 2 onto the operating part 30 using the same hand 36, and, when a longitudinal position is reached in which the surgeon wishes to immobilize the shaft 2, the locking mechanism can be activated by release of the shaft 2, and the shaft 2 can thus be blocked. Further functions of the endoscopic system are controlled by actuation of further operating elements, which can be arranged on the operating part 30, on a further operating part not shown in the figures, or on the control device, for example irrigation and suction functions by control of suitable valves, the function of endoscopic work instruments by control of corresponding motor drives, or the taking, processing, displaying and storing of endoscopic images by control of the light source, of the video camera and of an image processing, displaying and storing device. During the endoscopic procedure, the part of the shaft 2 remaining outside the patient 40 is enclosed by the shaft protection film 16, except for the portion located in the distal direction from the tube holder 26; this portion does not come into contact with the environment (see FIG. 1).

During the removal of the shaft 2 from the cavity inside the body of the patient 40, the shaft protection film 16 arranges itself automatically around the part of the shaft 2 guided through the shaft stop 20. After complete removal of the shaft 2, the shaft protection film 16, for this purpose having a suitable surplus length, can be pulled over the distal end 5 of the shaft 2, such that the shaft 2 is now completely enclosed by the shaft protection film. Transporting the endoscope 1 for cleaning is made easier in this way, and contamination of the shaft stop 20, of the operating part 30 and of the patient support 22 is avoided.

For the sake of clarity, not all reference signs are shown in all of the figures. Reference signs that are not explained in connection with one figure have the same meaning as in the other figures.

LIST OF REFERENCE SIGNS 1 endoscope
2 shaft
3 proximal end
4 endoscope box
5 distal end
6 endoscope lens
7 distal end portion
8 video connection
9 opening
10 work channel guide
11 housing
12 rotary bearing
13 drive
14 retaining arm
15 connecting portion
16 shaft protection film
17 rotary lever
18, 18', 18'', 18''' connections
19 coupling
20 shaft stop
21 mount
22 patient support
23 pressure plate
23' swivel arm
24 counter-pressure plate
25 bow
25' rubber band
26 tube holder
27 retainer bushing
28 fork
29 notch
30 operating part
31 menu control
32 carrier
33 joystick
34 half-shell
35 pressure sensor
36 hand
37 cable
40 patient 41 supply adapter
42 seat
43 video socket
44 coupling connection
45 light outlet

The invention claimed is:

1. An endoscopic system comprising:
a flexible endoscope with;
an elongate, flexible shaft,
a regulator part, and also
an operating part which can be placed on or pushed onto the shaft and which has at least one control element,
wherein the endoscopic system comprises;
a shaft stop,
which can be secured on a patient support, and
which has a locking mechanism, controllable by the at least one control element, for locking the shaft against movement in a longitudinal direction of the shaft;
wherein the at least one control element is a shaft sensor, and the locking mechanism can be controlled by the shaft sensor in such a way that, when a signal of the shaft sensor indicates that the operating part is not placed on or pushed onto the shaft, the shaft is locked.

2. The endoscopic system according to claim 1, wherein the operating part has a half-shell for receiving the shaft.

3. The endoscopic system according to claim 1, wherein the shaft sensor is a pressure sensor.

4. The endoscopic system according to claim 1, wherein the at least one control element is an operating element for manually controlling the locking mechanism.

5. The endoscopic system according to claim 4, wherein the shaft sensor, the operating element and the locking mechanism are connected in such a way that the locking mechanism can be controlled by the operating element only when the signal of the shaft sensor indicates that the operating part is placed on or pushed onto the shaft.

6. The endoscopic system according to claim 1, wherein the operating part has at least one operating element for controlling an angle of a distal end portion of the shaft.

7. The endoscopic system according to claim 1, wherein the operating part is designed to control endoscopic work instruments, or a further operating part is provided to control endoscopic work instruments.

8. The endoscopic system according to claim 1, wherein the locking mechanism can be controlled via a wireless connection.

9. The endoscopic system according to claim 1, wherein the shaft stop has a through-opening for holding the shaft.

10. The endoscopic system according to claim 1, wherein the shaft stop has a tube holder for holding a shaft protection film.

11. The endoscopic system according to claim 1, wherein the regulator part comprises at least one connection for supplying the endoscope, and/or at least one drive coupling for drives that adjust an angle of a distal end portion of the shaft of the endoscope.

12. The endoscopic system according to claim 1, wherein the shaft is connected to the regulator part so as to be rotatable about a longitudinal axis of the shaft.

13. The endoscopic system according to claim 1, wherein the shaft of the endoscope includes a shaft protection film on an outer portion of the shaft, and the shaft stop includes a tube holder;
the shaft protection film is pulled against the tube holder and is removable from the shaft when the shaft passes through the shaft stop in a direction toward a patient.

14. The endoscopic system according to claim 13, wherein the shaft protection film reattaches to the outer portion of the shaft when the shaft passes through the shaft stop in a direction opposite the patient.

15. The endoscopic system according to claim 13, wherein the shaft stop includes a bow configured to secure the shaft protection film to the tube holder.

16. The endoscopic system according to claim 1, wherein the locking mechanism for locking the shaft includes a first plate on a first side of the shaft and a second plate on a second side of the shaft;
the first plate is moveable in a direction towards the second plate locking the shaft against movement, and when the first plate is moveable in a direction opposite the second plate the shaft is able to pass through an opening between the first plate and the second plate.

* * * * *